(12) United States Patent
Boling et al.

(10) Patent No.: US 9,456,836 B2
(45) Date of Patent: Oct. 4, 2016

(54) APPARATUS AND METHOD FOR DELIVERING A NEUROSTIMULATOR INTO THE PTERYGOPALATINE FOSSA

(75) Inventors: Carl Lance Boling, San Jose, CA (US); Anthony V. Caparso, San Francisco, CA (US); Ryan Powell, Sunnyvale, CA (US); Jennifer Teng, Saratoga, CA (US); Morgan Clyburn, Menlo Park, CA (US)

(73) Assignee: AUTONOMIC TECHNOLOGIES, INC., Redwood City, CA (US)

( * ) Notice: Subject to any disclaimer, the term of this patent is extended or adjusted under 35 U.S.C. 154(b) by 157 days.

(21) Appl. No.: 13/476,224

(22) Filed: May 21, 2012

(65) Prior Publication Data

US 2012/0290057 A1 Nov. 15, 2012

Related U.S. Application Data

(63) Continuation-in-part of application No. 13/470,480, filed on May 14, 2012, now Pat. No. 9,220,524, which is a continuation-in-part of application No. 12/688,300, filed on Jan. 15, 2010, now Pat. No. 9,211,133.

(60) Provisional application No. 61/145,122, filed on Jan. 16, 2009.

(51) Int. Cl.
| | |
|---|---|
| *A61N 1/05* | (2006.01) |
| *A61B 17/24* | (2006.01) |
| *A61B 17/34* | (2006.01) |
| *A61N 1/36* | (2006.01) |
| *A61B 17/02* | (2006.01) |
| *A61B 17/3211* | (2006.01) |
| *A61B 17/32* | (2006.01) |
| *A61N 1/375* | (2006.01) |

(52) U.S. Cl.
CPC ........... *A61B 17/24* (2013.01); *A61B 17/3468* (2013.01); *A61B 17/02* (2013.01); *A61B 17/3211* (2013.01); *A61B 2017/320052* (2013.01); *A61N 1/0526* (2013.01); *A61N 1/0546* (2013.01); *A61N 1/0548* (2013.01); *A61N 1/36* (2013.01); *A61N 1/36057* (2013.01); *A61N 1/375* (2013.01)

(58) Field of Classification Search
CPC ............. A61N 1/0546; A61N 1/0548; A61N 1/37205; A61N 1/3606; A61N 1/36057; A61N 1/36; A61N 1/375; A61N 1/36017; A61B 17/24; A61B 1/018; A61B 17/3211; A61B 17/3468
USPC ........................... 607/2, 45, 46, 47, 115–118
See application file for complete search history.

(56) References Cited

U.S. PATENT DOCUMENTS

| | | | |
|---|---|---|---|
| 2004/0116977 A1* | 6/2004 | Finch | A61N 1/36017 607/46 |
| 2005/0059890 A1* | 3/2005 | Deal | A61B 1/018 600/433 |

(Continued)

*Primary Examiner* — Christopher D Koharski
*Assistant Examiner* — Pamela M Bays
(74) *Attorney, Agent, or Firm* — Tarolli, Sundheim, Covell & Tummino LLP

(57) ABSTRACT

One aspect of the present disclosure includes a neurostimulator delivery apparatus. The apparatus includes a handle portion, an elongate shaft extending from the handle portion, and a distal deployment portion. The distal deployment portion is configured to releasably mate with a neurostimulator. The neurostimulator is sized and configured for implantation into a craniofacial region of a subject.

12 Claims, 12 Drawing Sheets

(56) References Cited

U.S. PATENT DOCUMENTS

| | | | |
|---|---|---|---|
| 2006/0195169 A1* | 8/2006 | Gross et al. | ................ 607/116 |
| 2010/0114184 A1* | 5/2010 | Degtyar | ............. A61B 17/1659 606/86 R |
| 2010/0168513 A1* | 7/2010 | Pless et al. | .................. 600/106 |

* cited by examiner

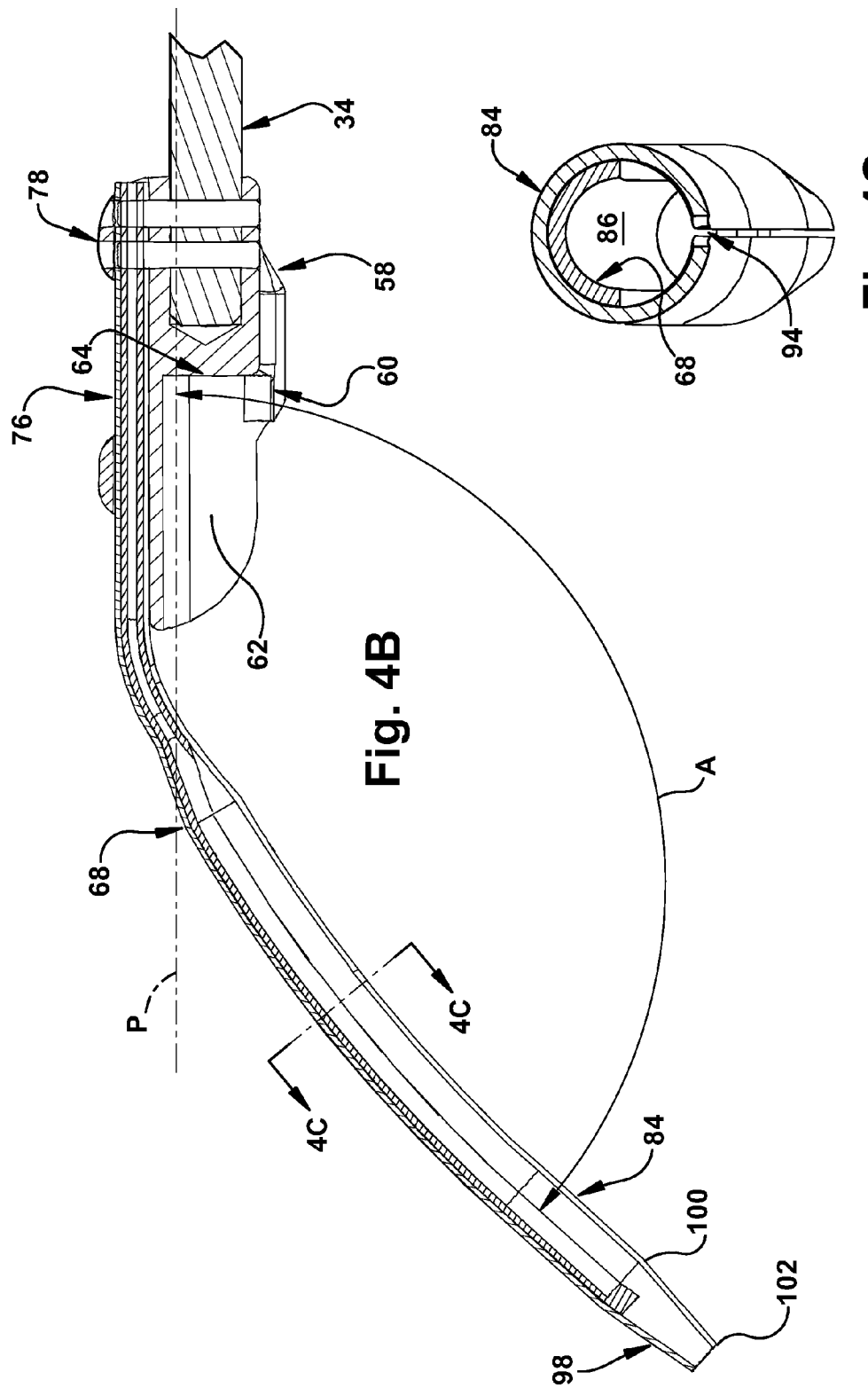

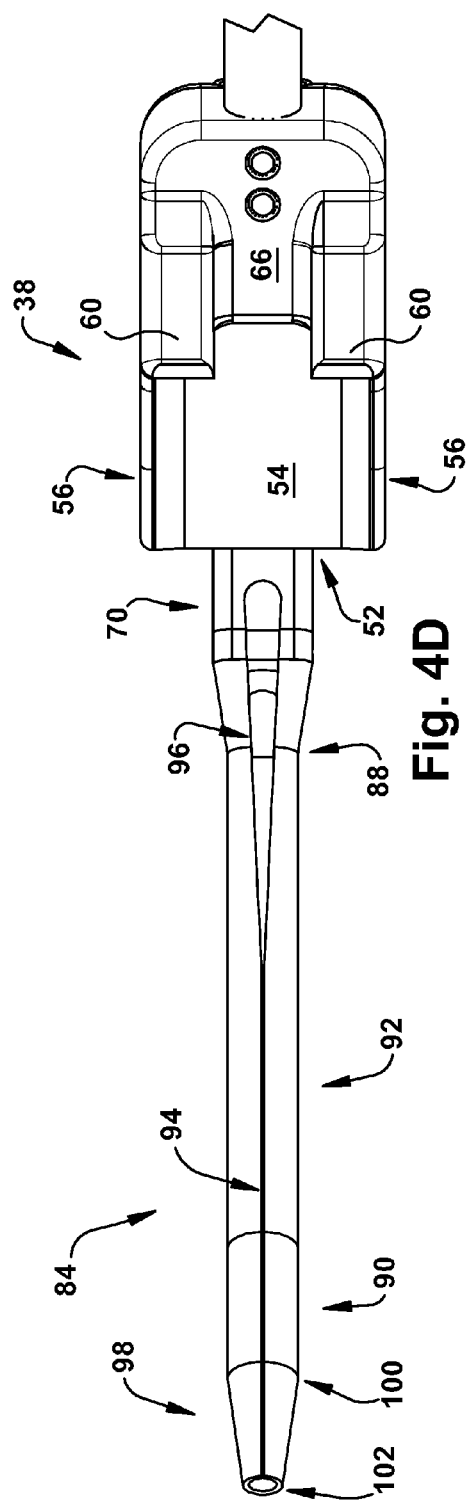
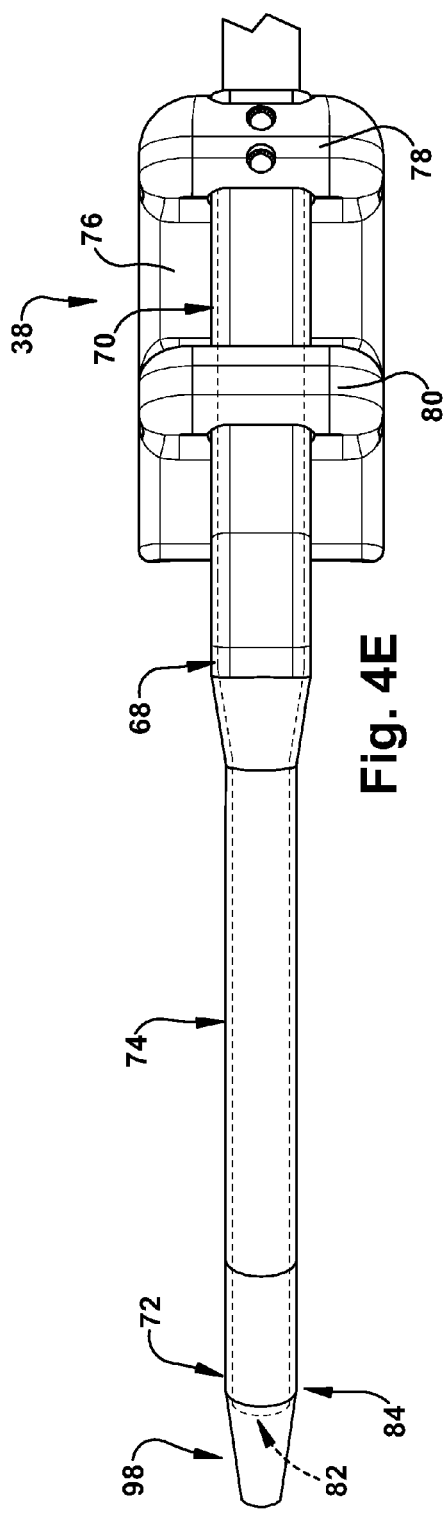

APPARATUS AND METHOD FOR DELIVERING A NEUROSTIMULATOR INTO THE PTERYGOPALATINE FOSSA

RELATED APPLICATIONS

This application is a continuation-in-part of U.S. patent application Ser. No. 13/470,480, filed May 14, 2012 now U.S. Pat. No. 9,220,524, which is a continuation-in-part of U.S. patent application Ser. No. 12/688,300, filed Jan. 15, 2010 now U.S. Pat. No. 9,211,133, which claims priority to U.S. Provisional Patent Application Ser. No. 61/145,122, filed Jan. 16, 2009. This application incorporates the above-identified applications herein by reference in their entirety, and claims priority to all aforementioned applications for all purposes.

TECHNICAL FIELD

The present disclosure relates generally to surgical tools configured to deliver medical devices to a craniofacial region of a subject, and more particularly to surgical tools configured to deliver an implantable neurostimulator to a pterygopalatine fossa of a subject.

BACKGROUND

Electrical stimulation of peripheral and central neural structures has shown increased interest due to the potential benefits it may provide to individuals suffering from many neurological and behavioral diseases. Many of these therapies today are not well accepted due to the invasive nature of the therapy, even though the efficacy is quite good. This has created a need for less invasive therapies that are directed toward patient and physician clinical needs.

Headaches are one of the most debilitating ailments that afflict millions of individuals worldwide. The specific pathophysiology of headaches is unknown. Known sources of headache pain consist of trauma, vascular, autoimmune, degenerative, infectious, drug and medication-induced, inflammatory, neoplastic, metabolic-endocrine, iatrogenic, musculoskeletal and myofacial causes. Also, even though the possible underlying cause of the headache pain is identified and treated, the headache pain may persist.

Currently, the sphenopalatine (pterygopalatine) ganglion (SPG) is a target of manipulation in clinical medicine to treat headaches. The SPG is an extracranial neuronal center located behind the nose. It consists of parasympathetic neurons that innervate (in part) the middle cerebral and anterior cerebral blood vessels, the facial blood vessels, and the lacrimal glands. The SPG also consists of sympathetic and sensory nerve fibers that pass through the SPG in route to their end organs. Manipulation of the SPG is mostly performed in attempted treatments of severe headaches, such as cluster headaches or migraines.

Various clinical approaches have been used for over 100 years to modulate the function of the SPG to treat headaches. These procedures vary from least invasive (e.g., transnasal anesthetic blocks) to much more invasive (e.g., surgical ganglionectomy), as well as procedures, such as surgical anesthetic injections, ablations, gamma knife and cryogenic surgery. These later procedures are very invasive, and most are non-reversible. In both cases, the surgical approach is typically through the nostrils or using a trans-coronoid notch approach.

SUMMARY

One aspect of the present disclosure includes a neurostimulator delivery apparatus. The apparatus includes a handle portion, an elongate shaft extending from the handle portion, and a distal deployment portion. The distal deployment portion is configured to releasably mate with a neurostimulator. The neurostimulator is sized and configured for implantation into a craniofacial region of a subject.

Another aspect of the present disclosure includes an apparatus configured to deliver a neurostimulator into a pterygopalatine fossa (PPF) of a subject. The apparatus includes a handle portion, an elongate shaft extending from the handle portion, an arcuate distal deployment member, and a central hub portion formed between the elongate shaft and the distal deployment member. The central hub portion is sized and configured to releasably mate with the neurostimulator (e.g., the neurostimulator body).

Another aspect of the present disclosure includes a method for deploying a neurostimulator in close proximity to a sphenopalatine ganglion (SPG) of a subject. One step of the method includes providing a neurostimulator delivery apparatus and a neurostimulator releasably coupled to the neurostimulator delivery apparatus. The neurostimulator delivery apparatus comprises a handle portion, an elongate shaft extending from the handle portion, and an arcuate distal deployment portion. The distal deployment portion is mated with a distal portion of a surgical tool already positioned in or about a craniofacial region. The neurostimulator is then manipulated so that an integral stimulation lead thereof progressively emerges from the distal deployment portion into close proximity with the SPG. Simultaneously, the neurostimulator delivery apparatus is withdrawn from the subject.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 4B is a cross-sectional side view of the distal end portion shown in FIG. 4A;

FIG. 4C is a cross-sectional view taken along Line 4C-4C in FIG. 4B;

FIG. 4D is a magnified top view of the distal end portion shown in FIG. 4A;

FIG. 4E is a bottom view of the distal end portion shown in FIG. 4D;

DETAILED DESCRIPTION

Figure 1A:
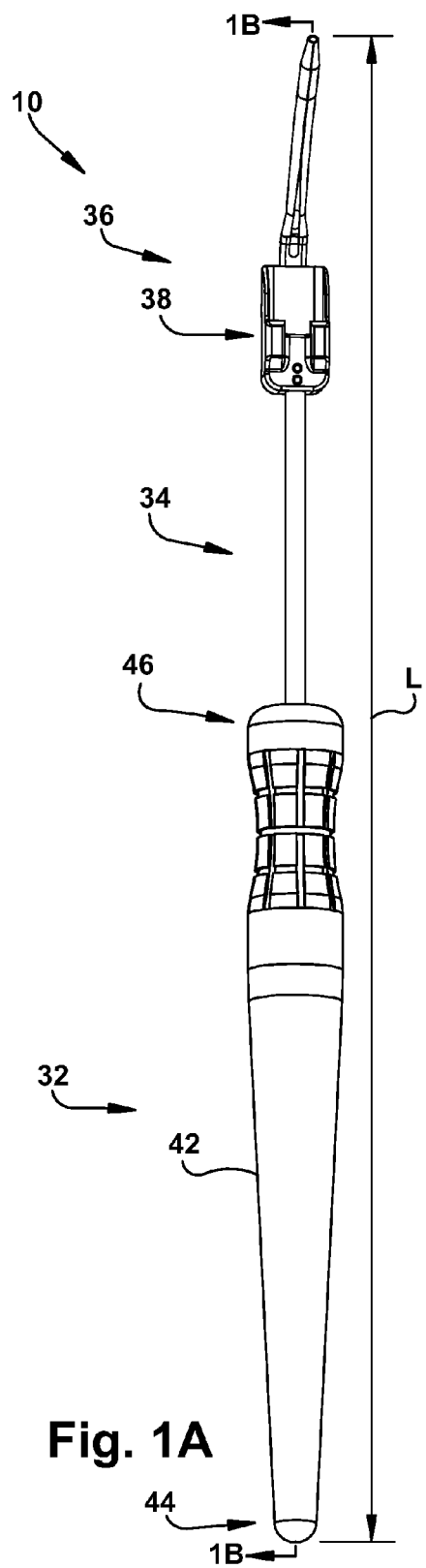
FIG. 1A is a top perspective view of an apparatus configured to deliver an implantable neurostimulator to a pterygopalatine fossa of a subject constructed in accordance with one aspect of the present disclosure.
Figure 1B:
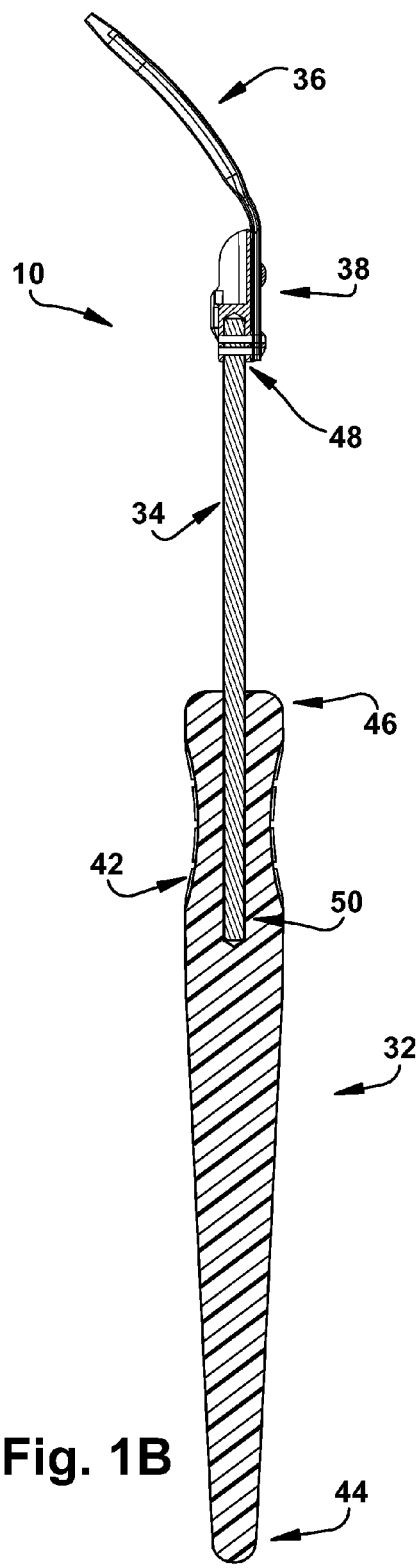
FIG. 1B is a cross-sectional side view of the apparatus in FIG. 1A.
Figure 2:
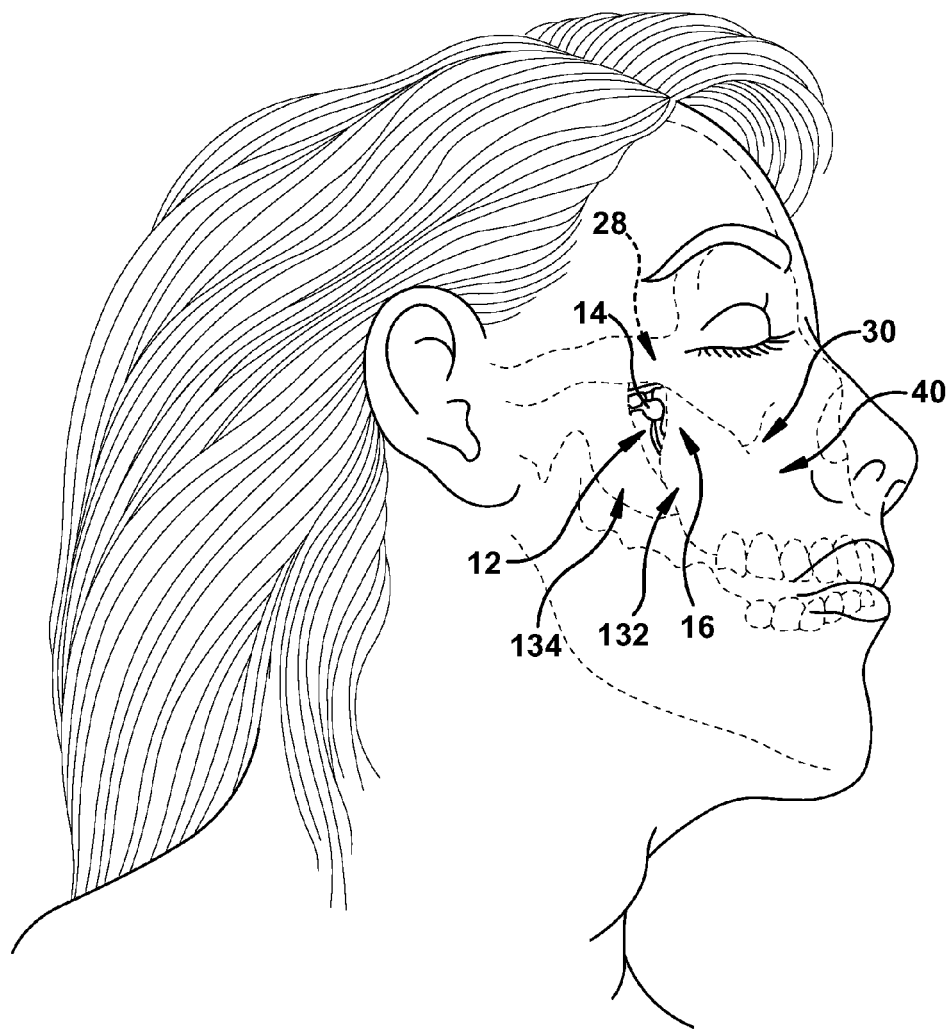
FIG. 2 is a perspective view showing part of the nervous innervations of the anterior craniofacial skeleton.

The present disclosure relates generally to surgical tools configured to deliver medical devices to a craniofacial region of a subject, and more particularly to surgical tools configured to deliver an implantable neurostimulator to a pterygopalatine fossa (PPF) of a subject. As representative of one aspect of the present disclosure, FIGS. 1A-B illustrate an apparatus 10 configured to deliver a neurostimulator into a craniofacial region, such as the PPF 12 (FIG. 2). The present disclosure may be employed to assist in treating a variety of chronic or acute medical conditions. Examples of such medical conditions can include, but are not limited to, pain (e.g., headache, facial pain, trigeminal neuralgias, sphenopalatine neuralgias and/or atypical face pain), movement disorders, epilepsy, cerebrovascular diseases, autoimmune diseases, sleep disorders, autonomic disorders, neurological disorders, urinary bladder disorders, abnormal metabolic states, disorders of the muscular system, and neuropsychiatric disorders.

Unless otherwise defined, all technical terms used herein have the same meaning as commonly understood by one of ordinary skill in the art to which the present invention pertains.

In the context of the present disclosure, the singular forms "a," "an" and "the" are intended to include the plural forms as well, unless the context clearly indicates otherwise. It will be further understood that the terms "comprises" and/or "comprising," as used herein, specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" should be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the term "headache" can refer to migraines, tension headaches, cluster headaches, trigeminal neuralgia, sphenopalatine neuralgia, secondary headaches, tension-type headaches, chronic and episodic headaches, medication overuse/rebound headaches, chronic paroxysmal hemicrinia headaches, hemicranias continua headaches, post-traumatic headaches, post-herpetic headaches, vascular headaches, reflex sympathetic dystrophy-related headaches, cervicalgia headaches, caroidynia headaches, sciatica headaches, trigeminal headaches, occipital headaches, maxillary headaches, chary headaches, paratrigeminal headaches, petrosal headaches, Sluder's headache, vidian headaches, low cerebrospinal fluid pressure headaches, temporomandibular joint (TMJ) headaches, causalgia headaches, myofascial headaches, all primary headaches (e.g., primary stabbing headache, primary cough headache, primary exertional headache, primary headache associated with sexual activity, hypnic headache, and new daily persistent headache), all trigeminal autonomic cephalagias (e.g., paroxysmal hemicranias, short-lasting unilateral neuralgiform headache attacks with conjunctival injection and tearing (SUNCT) and short-lasting unilateral neuralgiform headache attacks with cranial autonomic symptoms (SUNA)), chronic daily headaches, occipital neuralgia, atypical facial pain, neuropathic trigeminal pain, and miscellaneous-type headaches.

As used herein, the term "cluster headache" can refer to extremely painful and debilitating headaches that occur in groups or clusters. Cluster headaches can include chronic or episodic cluster headaches, cluster-type headaches, histamine headaches, histamine cephalalgia, Raedar's syndrome and sphenopalatine neuralgia.

As used herein, the term "migraine" can refer to an intense and disabling chronic or episodic headache typically characterized by severe pain in one or both sides of the head. Migraines can include, but are not limited to, migraine without aura, migraine with aura, migraine with aura but without headache, menstrual migraines, variant migraines, transformed migraines, menstrual migraine, complicated migraines, hemiplegic migraines, atypical migraines, chronic migraines, basilar-type migraines, childhood periodic syndromes that are commonly precursors of migraine (e.g., abdominal, cyclic vomiting, BPV, etc.), status migrainous, and all types of probable migraines.

As used herein, the term "facial pain" can refer to direct pain that typically involves nerves supplying the face or, alternatively, indirect (referred) pain from other structures in the head, e.g., blood vessels. The pain may be related to headache (e.g., migraine), muscular syndromes (e.g., TMJ), and herpetic or rheumatic disease or injury.

As used herein, the terms "modulate" or "modulating" can refer to causing a change in neuronal activity, chemistry and/or metabolism. The change can refer to an increase, decrease, or even a change in a pattern of neuronal activity. The terms may refer to either excitatory or inhibitory stimulation, or a combination thereof, and may be at least electrical, biological, magnetic, optical or chemical, or a combination of two or more of these. The terms can also be used to refer to a masking, altering, overriding, or restoring of neuronal activity.

As used herein, the term "close proximity" with reference to a portion of an electrode or electrical lead relative to a target nerve structure (e.g., sphenopalatine ganglia or SPG) can refer to a distance between the electrode (or electrical lead) and the target nerve structure sufficient to enable electrical modulation of the target nerve structure. Thus, in some instances, "close proximity" can refer to a distance between the electrode (or electrical lead) and the target nerve structure whereby the electrode (or electrical lead) is not in direct contact with the nerve structure, but electrical modulation of the target nerve structure is still possible. In one example, "close proximity" can mean that the distance between an electrode or electrical lead and a target nerve structure is less than 1 mm but direct contact between structures does not occur. In another example, "close proximity" can mean that the distance between an electrode or electrical lead and a target nerve structure is greater than 1 mm (e.g., about 1 mm to about 1 cm), but direct contact between structures does not occur.

As used herein, the term "subject" can refer to any warm-blooded organism including, but not limited to, human beings, pigs, rats, mice, dogs, goats, sheep, horses, monkeys, apes, rabbits, cattle, etc.

As used herein, the term "prevent" shall have its plain and ordinary meaning to one skilled in the art of pharmaceutical or medical sciences. For example, "prevent" can mean to stop or hinder a medical condition, such as a headache.

As used herein, the terms "treat" or "treating" shall have their plain and ordinary meaning to one skilled in the art of pharmaceutical or medical sciences. For example, "treat" or "treating" can mean to prevent or reduce a medical condition, such as a headache.

As used herein, the term "medical condition" can refer to pain, movement disorders, epilepsy, cerebrovascular diseases, autoimmune diseases, sleep disorders, autonomic disorders, urinary bladder disorders, abnormal metabolic states, disorders of the muscular system, infectious and parasitic diseases, neoplasms, endocrine diseases, nutritional and metabolic diseases, immunological diseases, diseases of the blood and blood-forming organs, mental disorders, diseases of the nervous system, diseases of the sense organs, diseases of the circulatory system, diseases of the respiratory system, diseases of the digestive system, diseases of the genitourinary system, diseases of the skin and subcutaneous tissue, diseases of the musculoskeletal system and connective tissue, congenital anomalies, certain conditions originating in the perinatal period, and symptoms, signs, and ill-defined conditions.

Pain treatable by the present invention can be caused by conditions including, but not limited to, migraine headaches, including migraine headaches with aura, migraine headaches without aura, menstrual migraines, migraine variants, atypical migraines, complicated migraines, hemiplegic migraines, transformed migraines, and chronic daily migraines, episodic tension headaches, chronic tension headaches, analgesic rebound headaches, episodic cluster headaches, chronic cluster headaches, cluster variants, chronic paroxysmal hemicranias, hemicrania continua, post-traumatic headache, post-traumatic neck pain, post-herpetic neuralgia involving the head or face, pain from spine fracture secondary to osteoporosis, arthritis pain in the spine, headache related to cerebrovascular disease and stroke, headache due to a vascular disorder, reflex sympathetic dystrophy, cervicalgia (which may be due to various causes including, but not limited to, muscular, discogenic or degenerative, including arthritic, posturally related or metastatic), glossodynia, carotidynia, cricoidynia, otalgia due to middle ear lesion, gastric pain, sciatica, maxillary neuralgia, laryngeal pain, myalgia of neck muscles, trigeminal neuralgia (sometimes also termed tic douloureux), post-lumbar puncture headache, low cerebro-spinal fluid pressure headache, TMJ joint disorder, atypical facial pain, ciliary neuralgia, paratrigeminal neuralgia (sometimes also termed Raeder's syndrome), petrosal neuralgia, Eagle's syndrome, idiopathic intracranial hypertension, orofacial pain, myofascial pain syndrome involving the head, neck and shoulder, chronic migraneous neuralgia, cervical headache, paratrigeminal paralysis, sphenopalatine ganglion neuralgia (sometimes also termed lower-half headache, lower facial neuralgia syndrome, Sluder's neuralgia and Sluder's syndrome), carotidynia, vidian neuralgia, causalgia, atypical odontalgia, cluster tic syndrome, geniculate neuralgia, glossopharyngeal neuralgia, occipital neuralgia and temporal arteritis and/or a combination of the above.

Movement disorders treatable by the present invention may be caused by conditions including, but not limited to, Parkinson's disease, cerebropalsy, dystonia, essential tremor and hemifacial spasms.

Epilepsy treatable by the present invention may be, for example, generalized or partial.

Cerebrovascular disease treatable by the present invention may be caused by conditions including, but not limited to, aneurysms, strokes, and cerebral hemorrhage.

Autoimmune diseases treatable by the present invention include, but are not limited to, multiple sclerosis.

Sleep disorders treatable by the present invention may be caused by conditions including, but not limited to, circadian rhythm disorders, sleep apnea and parasomnias.

Autonomic disorders treatable by the present invention may be caused by conditions including, but not limited to, gastrointestinal disorders, including but not limited to gastrointestinal motility disorders, nausea, vomiting, diarrhea, chronic hiccups, gastroesphageal reflux disease, and hypersecretion of gastric acid, autonomic insufficiency, autonomic instability, excessive epiphoresis, excessive rhinorrhea, and cardiovascular disorders including, but not limited, to cardiac dysrythmias and arrythmias, hypertension, carotid sinus disease, Holmes-adie syndrome, orthostatic hypotension, striatonigral degeneration, vasovagal syncope, lyme disease and autonomic instability.

Neurological disorders treatable by the inventive method may be caused by conditions including, but not limited to: hemifacial spasm, Melkersson-Rosenthal Syndrome and Parry-Romberg syndrome.

Urinary bladder disorders treatable by the present invention may be caused by conditions including, but not limited to, spastic or flaccid bladder.

Abnormal metabolic states treatable by the present invention may be caused by conditions including, but not limited to, hyperthyroidism or hypothyroidism.

Disorders of the muscular system treatable by the present invention can include, but are not limited to, muscular dystrophy, and spasms of the upper respiratory tract and face.

Neuropsychiatric or mental disorders treatable by the present invention may be caused by conditions including, but not limited to, depression, schizophrenia, bipolar disorder, and obsessive-compulsive disorder.

A brief discussion of the pertinent anatomy and neurophysiology is provided to assist the reader with understanding the present invention. The autonomic nervous system innervates numerous pathways within the human body and consists of two divisions: the sympathetic and the parasympathetic nervous systems. The sympathetic and parasympathetic nervous systems are antagonistic in their action, balancing the other system's effects within the body. The sympathetic nervous system (SNS) usually initiates activity within the body, preparing the body for action, while the parasympathetic nervous system (PNS) primarily counteracts the effects of the SNS.

The SPG 14 (FIG. 2) are located on both sides of the head. It shall be assumed for the following discussion of the present invention that reference is being made to the SPG 14 located on the left side of the head. The SPG 14 is located behind the posterior maxilla 16 in the PPF 12, posterior to the middle nasal turbinate (not shown in detail). The SPG 14 is part of the parasympathetic division of the autonomic nervous system; however, the SPG has both sympathetic and parasympathetic nerve fibers, as well as sensory and motor nerve fibers either synapsing within the ganglion (e.g., parasympathetic) or fibers that are passing through the ganglion and not synapsing (e.g., sympathetic, sensory and motor).

The parasympathetic activity of the SPG 14 is mediated through the greater petrosal nerve (not shown), while the sympathetic activity of the SPG is mediated through the deep petrosal nerve (not shown), which is essentially an extension of the cervical sympathetic chain (not shown). Sensory sensations generated by or transmitted through the SPG 14 include, but are not limited to, sensations to the upper teeth, feelings of foreign bodies in the throat, and persistent itching of the ear. The SPG 14 transmits sensory information, including pain, to the trigeminal system via the maxillary division (not shown).

One aspect of the present disclosure includes an apparatus 10 (FIGS. 1A-B) configured to deliver a neurostimulator into a craniofacial region of a subject. In some instances, the neurostimulator can be configured for implantation in the PPF 12. In other instances, the neurostimulator is sized and configured for implantation on a posterior maxilla 16. A neurostimulator capable of being delivered by the apparatus 10 can generally include any active implantable medical device configured to deliver electrical stimulation, alone or in combination with other types of stimulation to tissue of a subject. The neurostimulator can further include any active implantable medical device configured for implantation for a relatively short period of time (e.g., to address acute medical conditions) or a relatively long period of time (e.g., to address chronic medical conditions). Additionally, the neurostimulator can include one or more elements used to record or monitor a physiological response of a subject's tissue (e.g., a delivered therapy), as well as one or more other components that interface with the patient's tissue (e.g., therapeutic agent delivery mechanisms, sensors, etc.).

Figure 3:
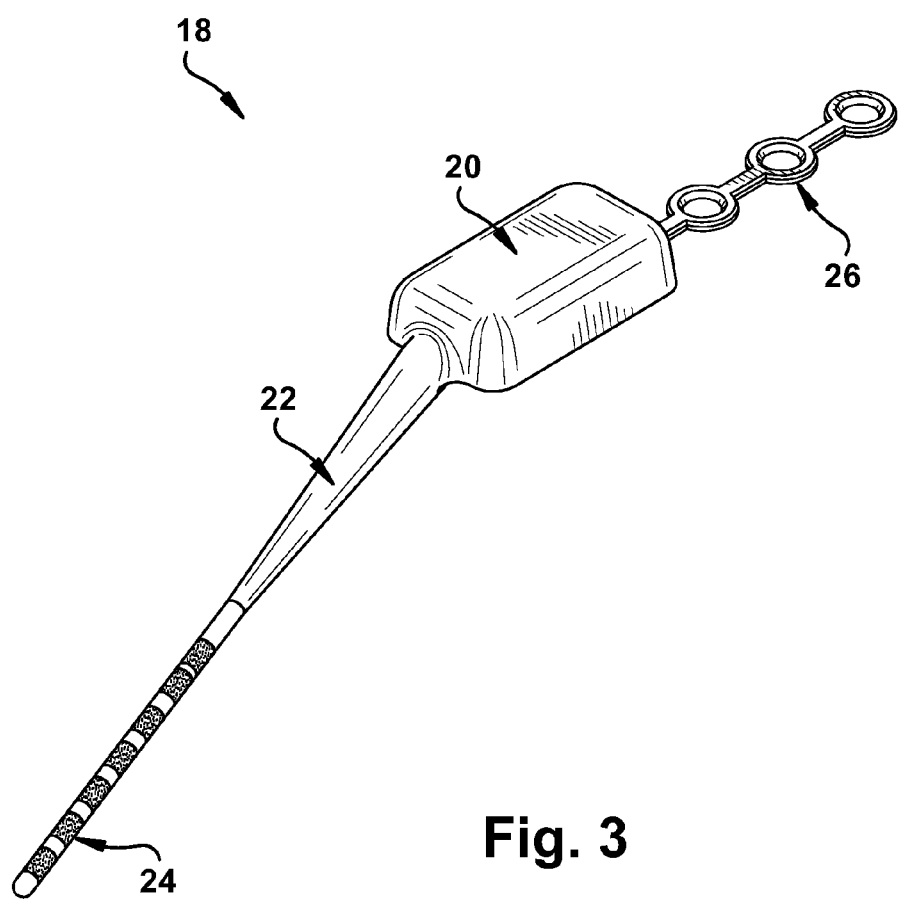
FIG. 3 is a perspective view of an implantable neurostimulator.

In one example of the present disclosure, a neurostimulator 18 can be configured as shown in FIG. 3 and disclosed in U.S. patent application Ser. No. 12/765,712 (hereinafter, "the '712 application"), the entirety of which is hereby incorporated by reference. Briefly, the neurostimulator 18 can comprise a stimulator body 20, an integral stimulation lead 22, which includes one or more stimulating electrodes 24, and an integral fixation apparatus 26. The neurostimulator 18 can be implanted as disclosed in the '712 application, i.e., such that the stimulator body 20 is positioned sub-periosteally medial to the zygoma 28 (FIG. 2) on the posterior maxilla 16 within the buccal fat pad (not shown) of the cheek, and the integral fixation apparatus 26 (FIG. 3) is anchored to the zygomaticomaxillary buttress 30 (FIG. 2) such that the integral stimulation lead 22 (FIG. 3) is placed within the PPF 14 (FIG. 2) or, more specifically, in close proximity (e.g., about 1-5 mm) to the SPG 14.

The neurostimulator delivery apparatus 10 (FIGS. 1A-B) of the present disclosure is designed and configured to facilitate delivery of a neurostimulator 18 in close proximity to the SPG 14 (FIG. 2) so that targeted electrical stimulation or delivery of electrical current from the neurostimulator to the SPG can be accomplished. Although reference below is made to the neurostimulator 18 in FIG. 3, it shall be appreciated that any variety of neurostimulator may be used as part of the present disclosure. As shown in FIGS. 1A-B, the neurostimulator delivery apparatus 10 comprises a handle portion 32, an elongated shaft 34 extending from the handle portion, a distal deployment member 36, and a central hub portion 38 formed between the elongated shaft and the distal deployment member. As described in more detail below, the neurostimulator delivery apparatus 10 is designed and configured to be inserted trans-orally from an incision located on the posterior maxilla 16 (FIG. 2).

In another aspect, the handle portion 32 (FIGS. 1A-B) and the elongated shaft 34 collectively define a longitudinal plane P that extends between the handle portion and the elongated shaft. The neurostimulator delivery apparatus 10 can have a length L of about 10 cm to about 30 cm. In one example, the neurostimulator delivery apparatus 10 can have a length L of about 14 cm. All or only a portion of the neurostimulator delivery apparatus 10 can be made of a rigid or semi-rigid medical grade metal or metal alloy, such as titanium or stainless steel, medical grade plastics (e.g., PEEK, polycarbonate, nylon), glass, ceramics (e.g., aluminum, zirconium oxide), combinations of metals, ceramics, plastics or plastic composites, and the like.

In another aspect, the handle portion 32 includes an ergonomic handle 42. The handle 42 can have a length of about 6 cm to about 12 cm, and vary in diameter from a proximal end 44 (e.g., about 0.5 cm to about 3 cm) to a distal end 46 (e.g., about 0.5 cm to about 2 cm) thereof. The handle 42 can include various features to provide grip and tactile maneuverability, such as circumferential ridges or a crosshatched precut pattern into the material forming the handle. The handle 42 can be made of a rigid or semi-rigid medical grade metal or metal alloy, such as stainless steel, medical grade plastics, polymers, and the like.

In another aspect, the elongated shaft 34 includes oppositely disposed first and second ends 48 and 50 that are securely connected to, or integrally formed with, the central hub portion 38 and the distal end 46 of the handle 42, respectively. The elongated shaft 34 can have any desired length and diameter. In some instances, the length of the elongated shaft 34 can be about 3 cm to about 7 cm. In one example, the length of the elongated shaft 34 can be about 4.5 cm. The diameter of the elongated shaft 34 can be about 0.1 cm to about 1 cm. In one example, the diameter of the elongated shaft 34 can be about 0.3 cm. In some instances, the diameter of the elongated shaft 34 can be uniform between the first and second ends 48 and 50. In other instances, the diameter of the elongated shaft 34 can taper from the first end 48 to the second end 50 (or vice-versa). The elongated shaft 34 can be made of a rigid or semi-rigid medical grade metal or metal alloy, such as stainless steel, medical grade plastics, polymers, or the like.

In another aspect, the central hub portion 38 (FIGS. 4A-B) is located between the elongated shaft 34 the distal deployment member 36. The central hub portion 38 is configured to allow the integral fixation apparatus 26 to be formed to the craniofacial anatomy and the neurostimulator 18 then loaded onto the neurostimulator delivery apparatus 10 prior to implantation, which reduces interference (of the integral fixation apparatus) with the apparatus and implant procedure. This feature of the central hub portion 38 facilitates fixation of the neurostimulator 18 to the curvature of the skull once the neurostimulator is released from the neurostimulator delivery apparatus 10.

Figure 4A:
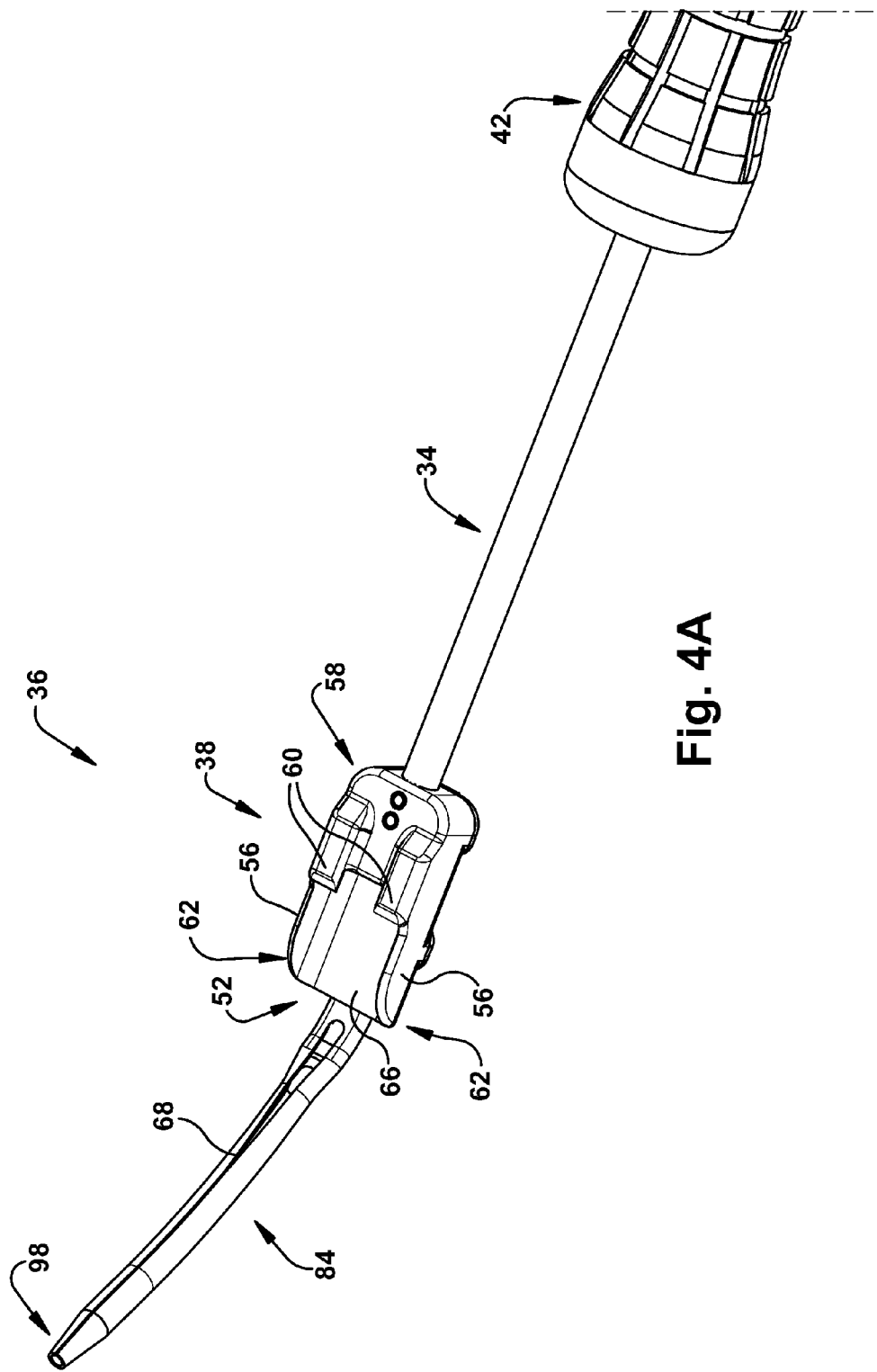
FIG. 4A is a schematic illustration showing a distal end portion of the apparatus in FIGS. 1A-B.

The central hub portion 38 is sized and configured to releasably mate with a neurostimulator 18. As shown in FIGS. 4A-B, the central hub portion 38 includes a port 52 configured to slidably receive a stimulator body 20 of the neurostimulator 18. The port 52 is defined by a lower surface 54, which is integrally formed with oppositely disposed side walls 56, as well as an upper portion 58 that includes a plurality of tangs 60. Although not shown, it will be appreciated that the upper portion 58 can include only one tang 60.

The lower surface 54 can be sized and dimensioned to allow the central hub portion 38 to releasably mate with the neurostimulator 18. In one example, the lower surface 54 can have a length of about 0.5 cm to about 2 cm (e.g., about 1 cm). In another example, the lower surface 54 can have a width of about 0.5 cm to about 2 cm (e.g., about 1 cm). Each of the oppositely disposed side walls 56 can have any desired height, such as about 0.1 cm to about 0.5 cm (e.g., about 0.3 cm). As shown in FIGS. 4A-B, each of the side walls 56 can have a contoured arcuate portion 62.

The tangs 60, in addition to the lower surface 54 and the side walls 56 are configured to provide a retention force when the stimulator body 20 is received in the port 52. Each of the tangs 60 includes an overhang portion 64 for contacting a portion of the stimulator body 20 (e.g., when the neurostimulator 18 is disposed in the port 52). Each of the overhang portions 64 permits the amount of a retention force between the stimulator body 20 and the central hub portion 38 to be selectively adjusted. For example, bending of the integral fixation apparatus 26 of the neurostimulator 18 towards a surface 66 of the upper portion 58 creates opposing forces between the overhang portions 64 and a surface of the stimulator body 20. Increasing an adjustment angle of the integral fixation apparatus 26 towards the surface 66 results in an increased retention force. Removal of the retention force during retraction requires the integral fixation apparatus 26 to be pushed away from the surface 66.

The central hub portion 38 can be made of a rigid or semi-rigid medical grade metal or metal alloy, such as stainless steel, medical grade plastics, polymers, or the like. The central hub portion 38 is configured to hold or carry the neurostimulator body 20 during placement of the neurostimulator 18. Thus, one skilled in the art will appreciate that the amount of material used to form the central hub portion 38 should be minimized to reduce the amount of tissue dissection needed to place the neurostimulator 18 in vivo, as well as to reduce the amount of drag that occurs during placement and removal of the neurostimulator delivery apparatus 10.

In another aspect, the distal deployment member 36 (FIGS. 4B-E) comprises a spine member 68 that extends from, and is securely connected to, the central hub portion 38. The spine member 68 (FIG. 4E) has an elongated configuration and includes a proximal end portion 70, a distal end portion 72, and an intermediate portion 74 extending between the proximal and distal end portions. The proximal end portion 70 is securely connected to a bottom surface 76 of the central hub portion 38. In one example, the proximal end portion 70 can extend through first and second arch members 78 and 80, each of which is integrally formed with the bottom surface 76.

Figure 5A:
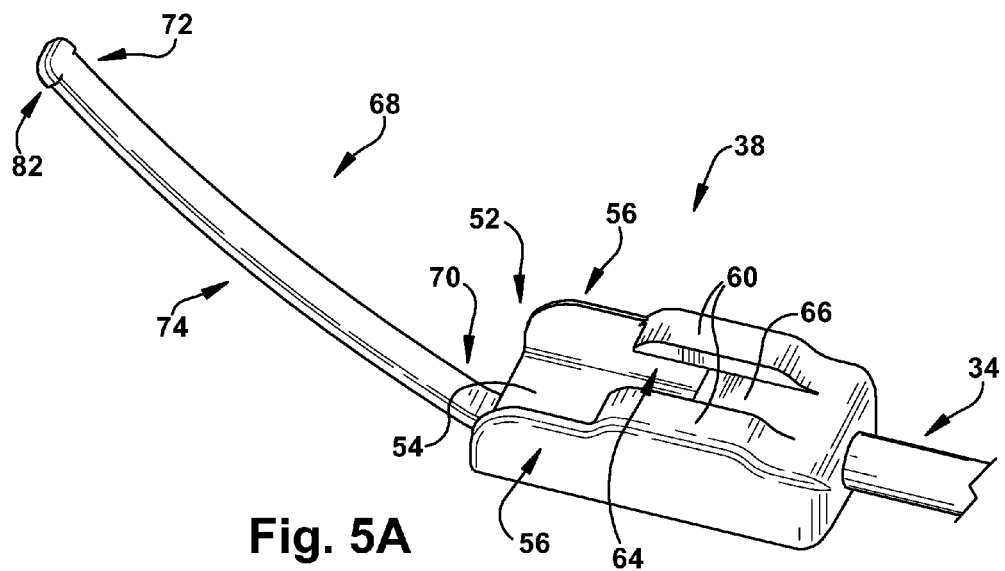
FIG. 5A is a magnified perspective view showing a spine member and a central hub portion of the distal end portion in FIG. 4A.

The spine member 68 can have any desired length and width. In one example, the spine member 68 can have a length of about 4 cm to about 6 cm (e.g., about 5 cm). In another example, the spine member 68 can have a width of about 0.1 cm to about 0.8 cm (e.g., about 0.3 cm). The spine member 68 can have a uniform width or, as shown in FIG. 4E, the width of the spine member can taper from a first width at the proximal end portion 70 that is greater than a second width at the distal end portion 72. In some instances, a distal tip 82 of the spine member 68 can include a tapered arcuate end as shown in FIG. 4E. In other instances, the distal tip 82 of the spine member 68 can be bulbous or mushroom-shaped (FIG. 5A).

In some instances, the distal end portion 72 of the spine member 68 can extend at an angle A (FIG. 4B) relative to the longitudinal plane P of the neurostimulator delivery apparatus 10. In one example, the angle A can be about 10° to about 45°, depending upon the craniofacial anatomy of the subject. In other instances, the spine member 68 can have a semi-circular or flattened cross-sectional profile. In one example, the spine member 68 can have a cross-sectional profile configured to correspond to the rounded outer surface of the integral stimulation lead 22, e.g., to accept and mate with the integral stimulation lead.

The spine member 68 can have a rigid, semi-rigid, or flexible configuration. The spine member 68 can be made from one or combination of rigid, semi-rigid, or flexible materials, such as metals, metal alloys, and polymers or plastics. In some instances, all or only a portion of the spine member 68 can be malleable. For example, only the distal end portion 72 of the spine member 68 can be malleable. In another example, the spine member 68 can be made of a malleable metal that supports a splittable sheath 84 and the integral stimulation lead 22 from buckling when longitudinal or lateral forces are encountered. The malleability allows a physician to conform the shape of the neurostimulator 18 (e.g., the integral stimulation lead 22) to correspond to a patient's anatomy and thereby aid with implantation. Malleability in some cases is not required; thus, a spine member 68 made from a non-malleable material, such as plastic can also serve the intended function.

In another aspect, the distal deployment member 36 further includes a splittable sheath 84 securely disposed about a portion of the spine member 68. As shown in FIG. 4B, for example, the splittable sheath 84 extends about the distal end portion 72 of the spine member 68. The splittable sheath 84 has a substantially C-shaped cross-sectional profile that defines a first lumen 86, which is configured to receive an integral stimulation lead 22 of the neurostimulator 18. The splittable sheath 84 can be securely connected to the spine member 68 by any one or combination of attachment mechanisms, such as adhesives, pins, staples, etc. In some instances, the splittable sheath 84 can be made of a semi-flexible material (or materials). In one example, the splittable sheath 84 can be formed from a plastic or polymer, such as polytetrafluoroethylene. In other instances, the splittable sheath 84 can be formed from a flexible material having a thickness of about 0.04 inches to about 0.001 inches.

Referring to FIG. 4D, the splittable sheath 84 includes a proximal end portion 88, a distal end portion 90, and an intermediate portion 92 that extends between the proximal and distal end portions. The splittable sheath 84 includes a seam 94 that extends from the distal end portion 90 to an opening 96 at the proximal end portion 88. The seam 94 allows for removal or deployment of the integral stimulation lead 22 of the neurostimulator 18 from the splittable sheath 84 with minimal load on the integral stimulation lead. For instance, applying a tactile force to the handle 42 of the neurostimulator delivery apparatus 10 can cause the seam 94 to split and thereby release the integral stimulation lead 22 for positioning and implantation in the PPF 12. Undesirable loading on the integral stimulation lead 22 can cause migration of the lead away from the desired implant location during withdrawal of the neurostimulator delivery apparatus 10. Advantageously, only a portion of the splittable sheath 84 is parted during deployment of the neurostimulator 18, which reduces the load on the integral stimulation lead 22.

As shown in FIG. 4B and FIGS. 4D-E, the splittable sheath 84 includes a tapered distal end portion 98 that is unsupported by the spine member 68. In other words, the tapered distal end portion 98 is free from direct contact with the distal end portion 72 of the spine member 68. In some instances, the diameter of the tapered distal end portion 98 decreases from a first end 100 to a second end 102 thereof. In other instances, the diameter at the second end 102 of the tapered distal end portion 98 is less than the diameter at the first end 100 of the tapered distal end portion. In further instances, the diameter at a portion of the tapered distal end portion 98 is less than the diameter of the intermediate portion 92 and/or the proximal end portion 88 of the splittable sheath 84. The tapered distal end portion 98 of the splittable sheath 84 facilitates insertion of the neurostimulator 18 into areas of the craniofacial anatomy that are narrow or otherwise difficult to access. It will be appreciated that the spine member 68 can optionally extend to the tapered distal end portion 98 as well.

Figure 5B:
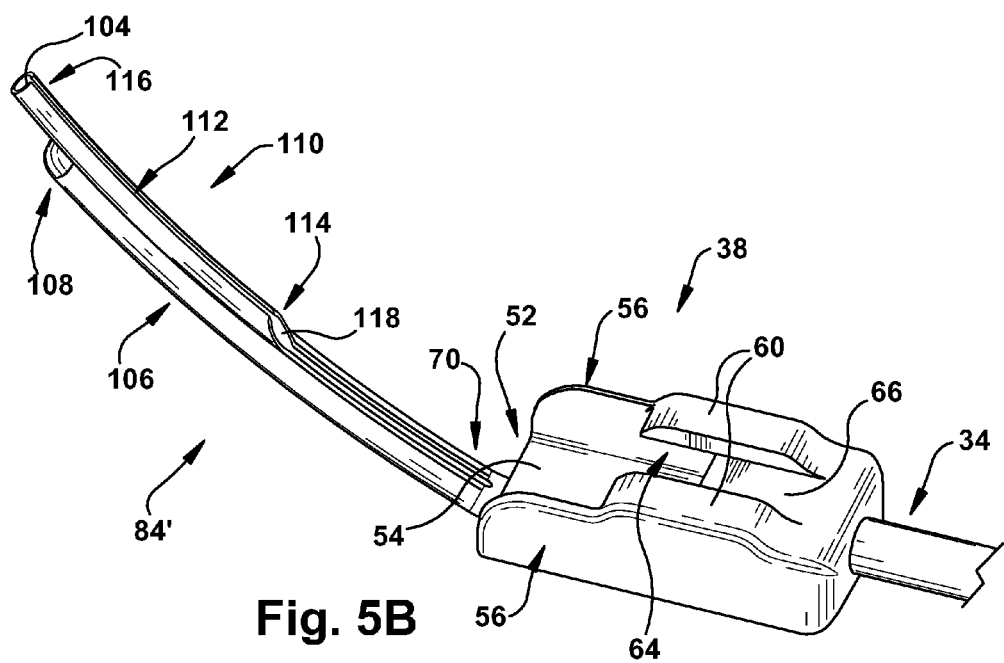
FIG. 5B is a magnified perspective view showing one configuration of a splittable sheath securely disposed about a portion of the spine member in FIG. 5A.
Figure 5C:
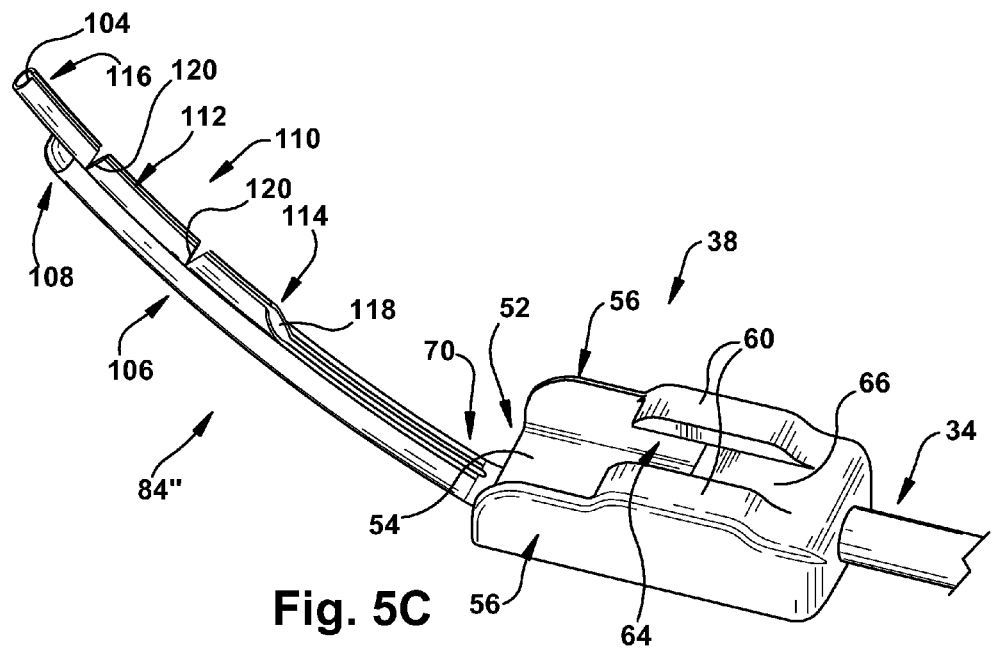
FIG. 5C is a magnified perspective view showing an alternative configuration of the splittable sheath in FIG. 5B.
Figure 5D:
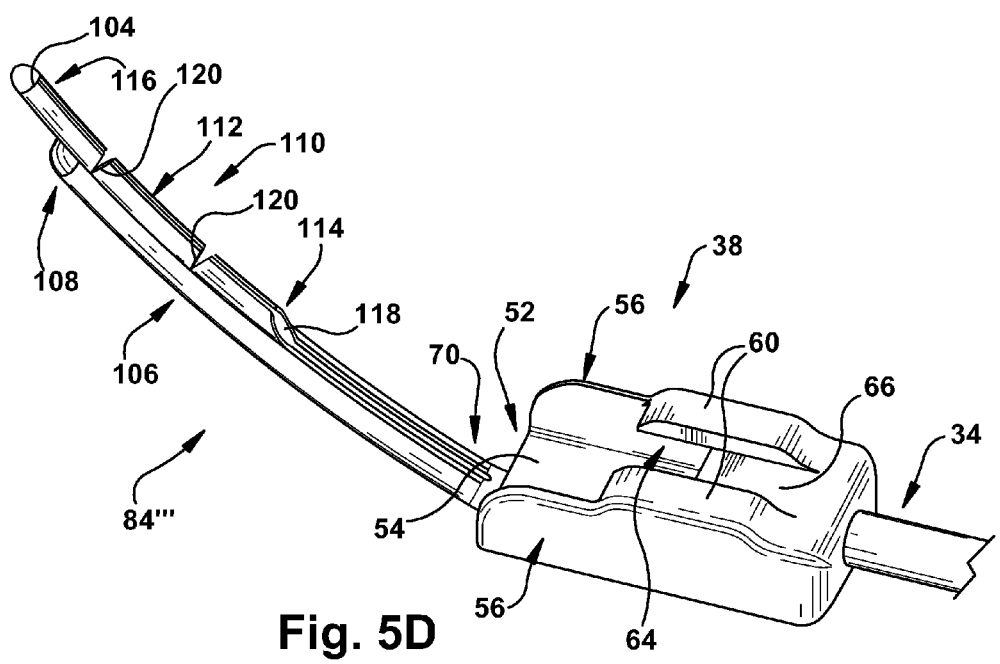
FIG. 5D is a magnified perspective view showing another alternative configuration of the splittable sheath in FIG. 5C.

Alternative configurations of the splittable sheath 84 are shown in FIGS. 5B-D. Except where described, the alternative configurations can be identically constructed as the splittable sheath 84 shown in FIGS. 4A-E and discussed above. In some instances, the splittable sheath 84' (FIG. 5B) can include a first lumen 86 configured to receive the spine member 68, and a second lumen 104 configured to receive an integral stimulation lead 22 of the neurostimulator 18. As shown in FIG. 5B, the first lumen 86 is defined by a first tubular sheath 106 configured to receive the spine member 68. Securely connected to a distal portion 108 of the first tubular sheath 106 is a second tubular sheath 110, which includes a seam 112 that extends between first and second ends 114 and 116 thereof. An opening 118 configured to receive the integral stimulation lead 22 of the neurostimulator 18 is located at the second end 116 of the second tubular sheath 110.

FIG. 5C illustrates an alternative configuration of the splittable sheath 84' shown in FIG. 5B. As shown in FIG. 5C, the second tubular sheath 110 can include one or more spaced apart radial slits 120. The radial slits 120 can be formed by cutting or piercing a portion of the side wall comprising the second tubular sheath 110. The presence of radial slits 120 reduces or prevents flaring of the second tubular sheath 110 at the seam 112, which can be caused by bending of the distal deployment member 36 (e.g., during implantation of the neurostimulator 18). The radial slits 120 can be located in parallel from one another (e.g., adjacent one another) or, alternatively, the radial slits can be located axially offset from one another on opposite sides of the seam 112. The radial slits 120 can have any desired cross-sectional profile (e.g., V-shaped, U-shaped, I-shaped, etc.), including any desired length and width. It will be appreciated that any number of radial slits 120 can be included as part of the second tubular sheath 110. Additionally, it will be appreciated that the splittable sheath 84 shown in FIGS. 1A-B can include one or more radial slits 120.

Another alternative configuration of the splittable sheath 84" in FIG. 5C is shown in FIG. 5D. The splittable sheath 84'" in FIG. 5D can be identically constructed as the splittable sheath 84" in FIG. 5C, except that the splittable sheath in FIG. 5D can include a tapered distal end portion 98. In some instances, the diameter of the tapered distal end portion 98 decreases from a first end 100 to a second end 102 thereof. In other instances, the diameter at the second end 102 of the tapered distal end portion 98 is less than the diameter at the first end 100. In further instances, the diameter at a portion of the tapered distal end portion 98 is less than the diameter of the first end 114 and/or the second end 116 of the second tubular sheath 110. The tapered distal end portion 98 of the second tubular sheath 110 can facilitate insertion of the neurostimulator 18 into areas of the craniofacial anatomy that are narrow or otherwise difficult to access.

Figure 6:
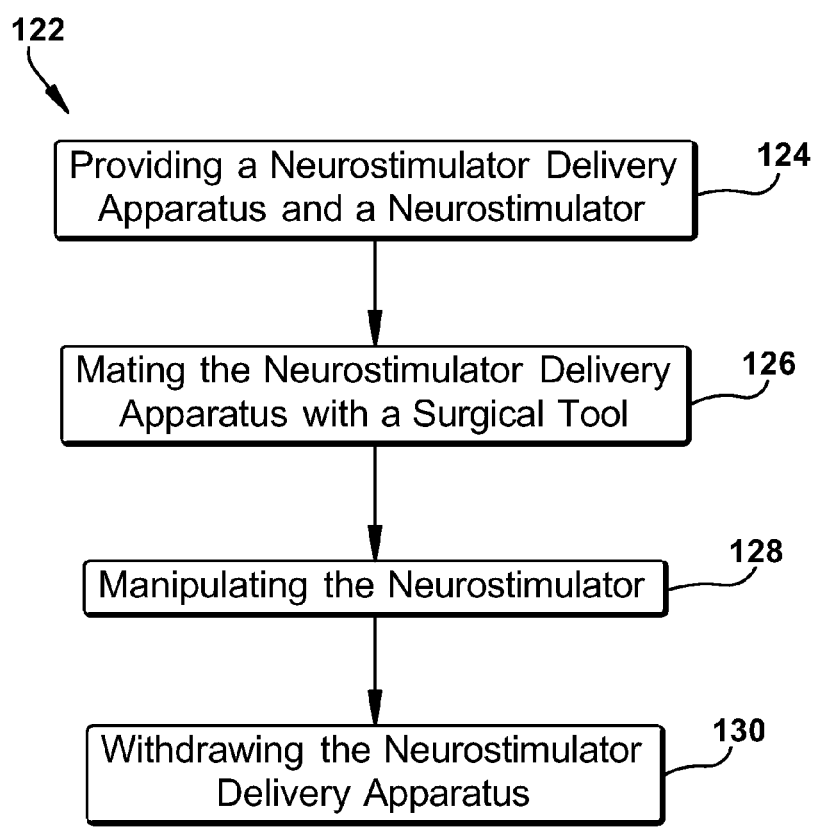
FIG. 6 is a process flow diagram illustrating a method for deploying a neurostimulator in close proximity to a sphenopalatine ganglion according to another aspect of the present disclosure.

Another aspect of the present disclosure is illustrated in FIG. 6 and includes a method 122 for deploying a neurostimulator 18 in close proximity to a SPG 14. At Step 124, a neurostimulator delivery apparatus 10 and a neurostimulator 18 are provided. In one example, the neurostimulator delivery apparatus 10 is configured as shown in FIGS. 1A-B and described above. In another example, the neurostimulator 18 is configured as shown in FIG. 3 and described in the '712 application.

Following Step 124, the neurostimulator delivery apparatus 10 can be used to deliver the neurostimulator 18 in close proximity to the SPG 14 as disclosed in U.S. patent application Ser. No. 13/470,480 (hereinafter, "the '480 application"). Briefly, an incision (not shown) is made at a gingival-buccal insertion site in a similar or identical manner as disclosed in U.S. Patent Publication No. 2010/0185258 A1, which is hereby incorporated by reference in its entirety. In one example, a #10 scalpel blade (not shown) can be used to make an incision in a horizontal manner between the second and third molars (not shown).

Next, a first surgical tool (not shown) similar or identical to the one disclosed in the '480 application is inserted into the incision and subperiosteally. In some instances, the anatomy of the subject's skull, including the location and size of the PPF 12 can be determined prior to insertion of the first surgical tool. After inserting the first surgical tool into the incision, the first surgical tool is urged in a posterior direction so that a first major surface of the surgical tool's distal portion traverses under the zygomatic bone 28 along the maxillary tuberosity 132. The first surgical tool is then advanced further until a distal dissecting tip thereof engages the junction formed by the posterior maxillary buttress (not shown) and the pterygoid plate 134, just inferior and lateral to the PPF 12. Advancement of the first surgical tool may naturally stop when the distal dissecting tip is correctly positioned at the junction formed by the posterior maxillary buttress and the pterygoid plate 134. The first surgical tool is then withdrawn, thereby creating a surgical access cavity (not shown).

Next, a second surgical tool 136 (not shown in detail) (FIG. 8) as disclosed in the '480 application is inserted into the surgical access cavity. After the second surgical tool 136 is appropriately positioned in the surgical access cavity, an electrode lead blank (not shown) is carefully inserted into an insertion groove of the second surgical tool 136 and progressively advanced along the insertion groove. The electrode lead blank can be configured to have the same or substantially the same dimensions as the integral stimulation lead 22 of the neurostimulator 18. The electrode lead blank is urged along the insertion groove until a distal end of the electrode lead blank extends from the surgical access cavity into close proximity with the SPG 14.

Figure 7A:
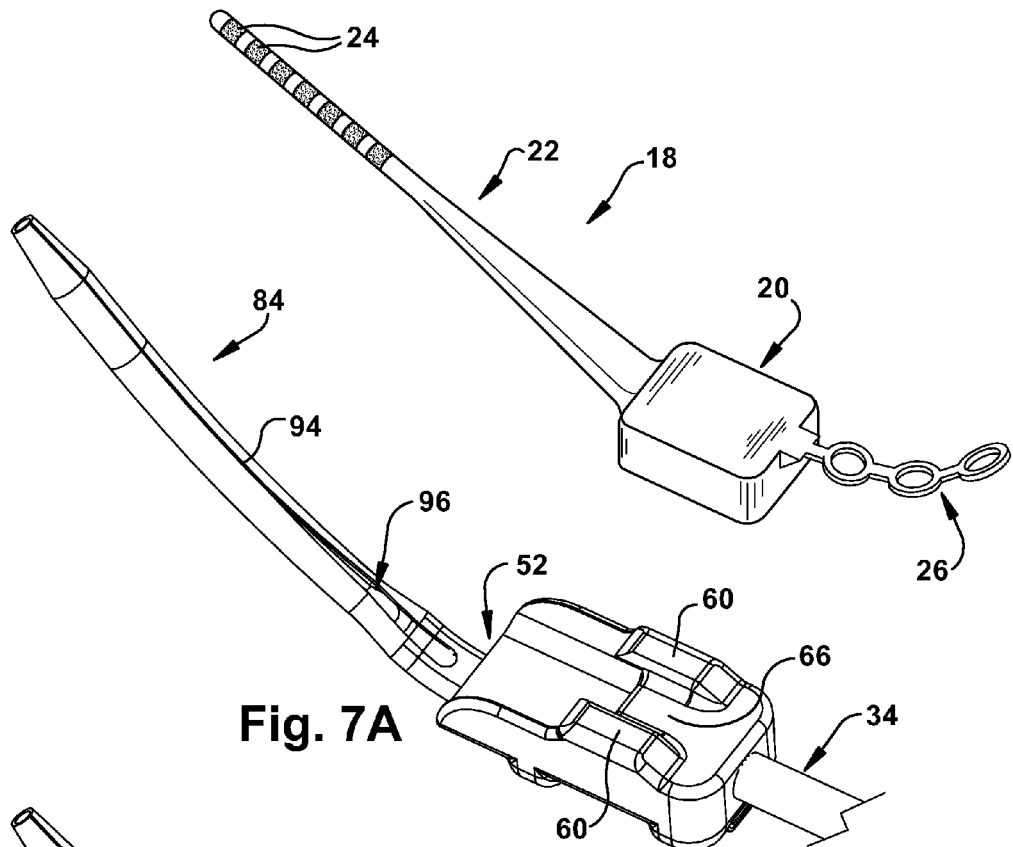
FIG. 7A is schematic illustrating showing the distal end portion of the apparatus in FIGS. 1A-B and the neurostimulator in FIG. 3.
Figure 7B:
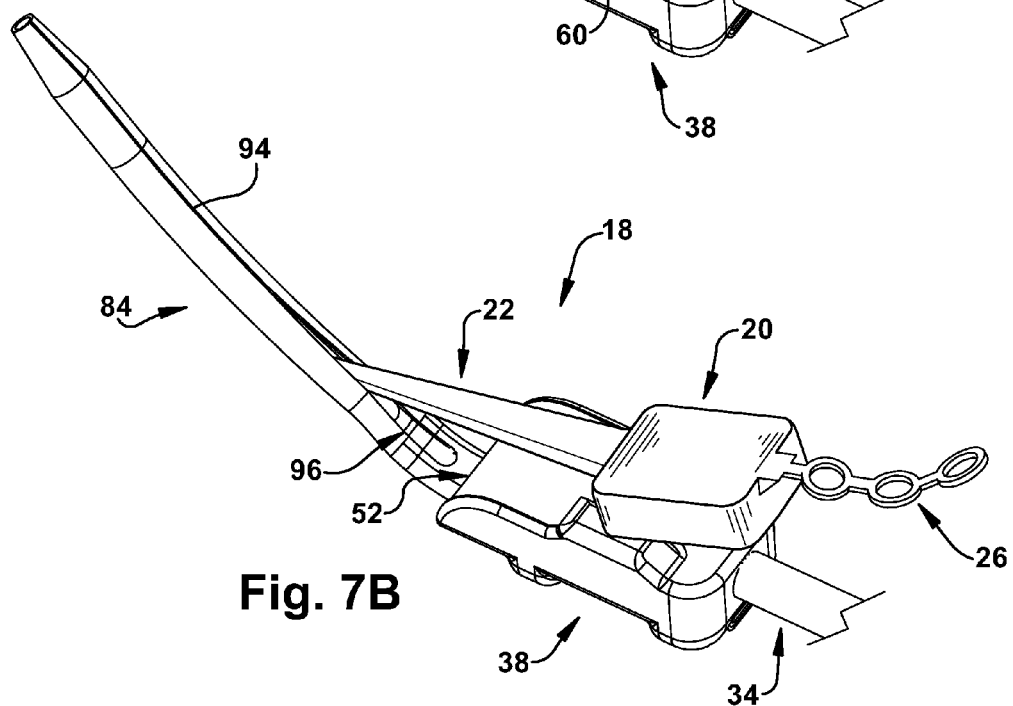
FIG. 7B is a schematic illustration showing an integral stimulation lead of the neurostimulator in FIG. 7A being loaded into a splittable sheath of the apparatus in FIGS. 1A-B.
Figure 7C:
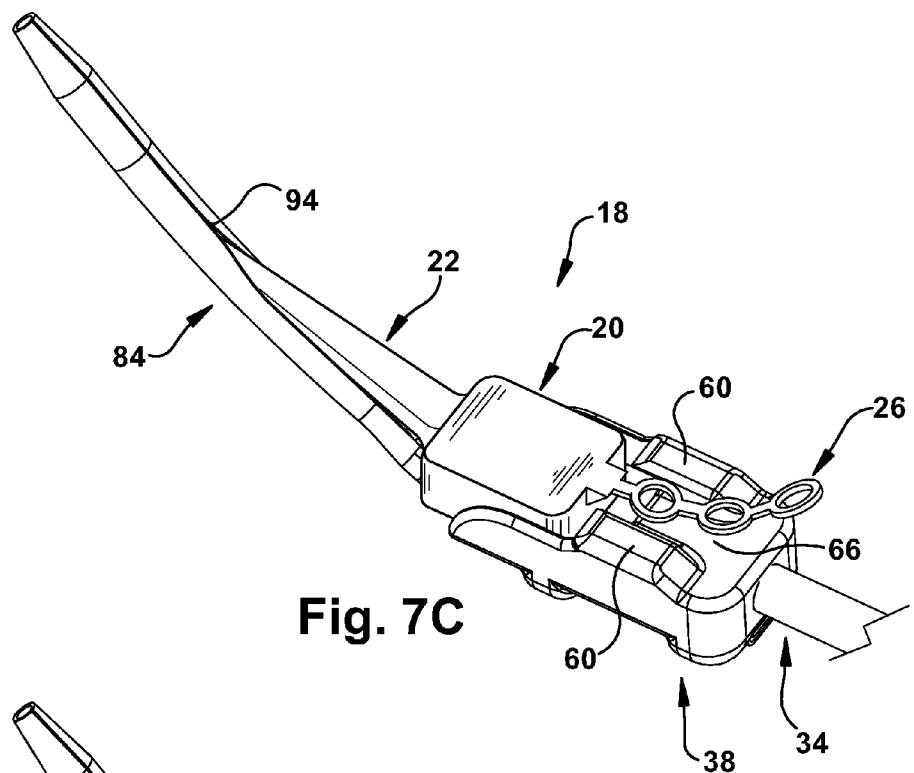
FIG. 7C is a schematic illustration showing the neurostimulator in FIG. 7B being seated within a central hub portion of the apparatus in FIGS. 1A-B.
Figure 7D:
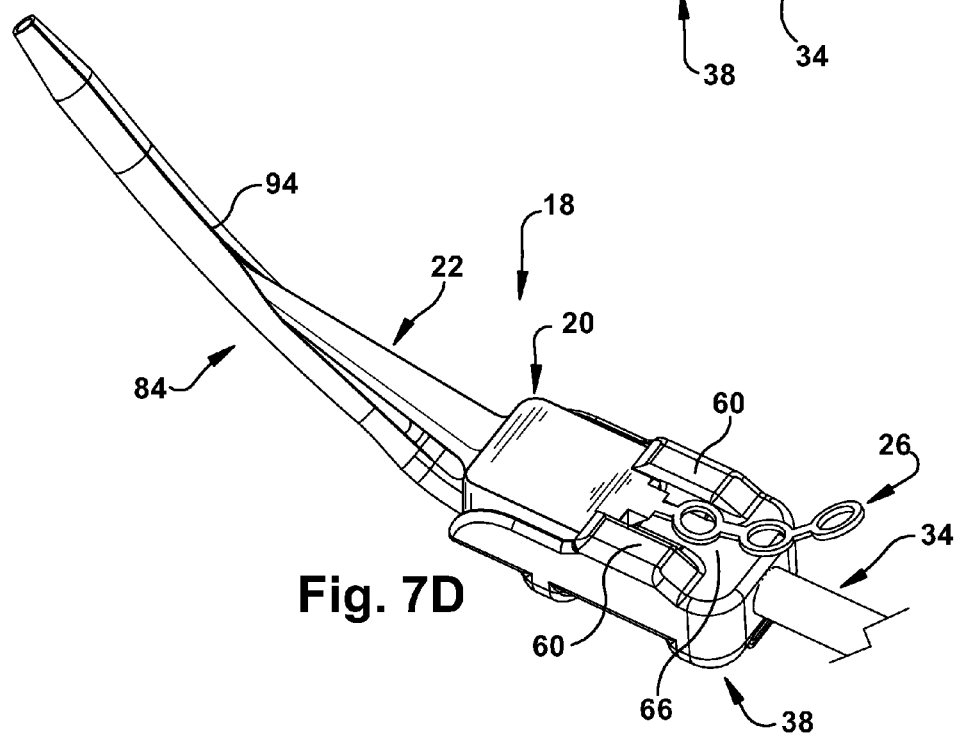
FIG. 7D is a schematic illustration showing the neurostimulator in FIG. 7B securely seated within the central hub portion.

Next, the electrode lead blank is removed from the subject. Either before, during, or after removal of the electrode lead blank, the neurostimulator 18 is mated with (e.g., loaded onto) the neurostimulator delivery apparatus 10 as shown in FIGS. 7A-D. To do so, the neurostimulator 18 is first brought into close proximity with the central hub portion 38 of the neurostimulator delivery apparatus 10 (FIG. 7A). The neurostimulator 18 is then angled slight downward toward the spine member 68 of the neurostimulator delivery apparatus 10 until a distal portion of the integral stimulator lead 22 is introduced or inserted into the opening 96 of the splittable sheath 84 (FIG. 7B). Next, the neurostimulator 18 is progressively advanced in a distal direction until a portion of the neurostimulator body 20 is in flush contact with the lower surface 54 of the central hub portion 38 (FIG. 7C). As shown in FIG. 7D, the neurostimulator 18 is then advanced towards the handle 42 of the neurostimulator delivery apparatus 10 until the neurostimulator body 20 snugly engages the tangs 60 and the integral fixation apparatus 26 engages the surface 66 of the central hub portion 38, thereby providing a retention force to keep the neurostimulator securely mated with the neurostimulator delivery apparatus 10 during implantation.

Figure 8:
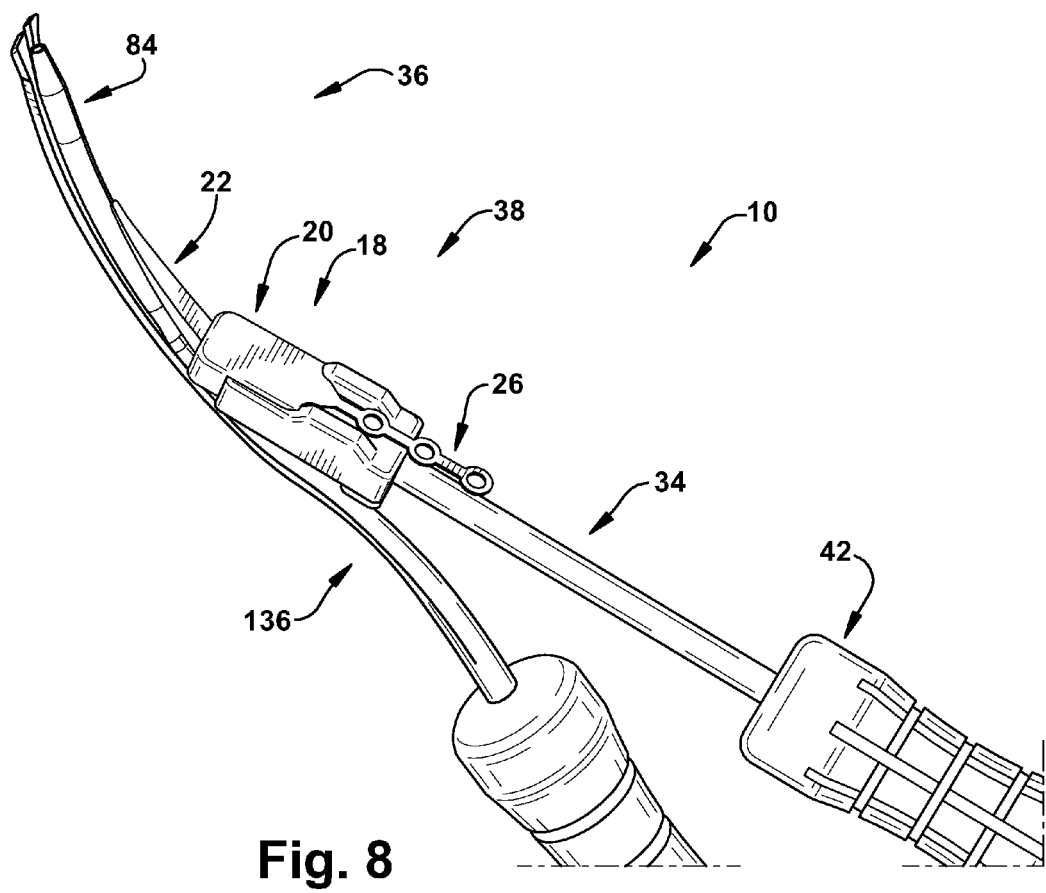
FIG. 8 is a schematic illustration showing the apparatus and neurostimulator in FIG. 7D being advanced along an insertion groove of a surgical tool.

At Step 126, the neurostimulator deployment apparatus 10 is mated with the second surgical tool 136 (FIG. 8). For example, the spine member 68 of the neurostimulator delivery apparatus 10 can slidably engage the insertion groove of the second surgical tool 136. Once the neurostimulator delivery device 10 is properly mated with the second surgical tool 136, the neurostimulator 18 is deployed from the neurostimulator delivery apparatus 10 (Step 128). The neurostimulator 18 can then be implanted within the subject as discussed above and disclosed in the '712 application. Following implantation of the neurostimulator 18, the neurostimulator delivery apparatus 10 can be withdrawn from the subject and the surgery completed (Step 130). With the neurostimulator 18 securely implanted within the subject, an electrical current from the neurostimulator can be applied to the SPG 14 to treat a medical condition (e.g., headache).

From the above description of the invention, those skilled in the art will perceive improvements, changes and modifications. Such improvements, changes and modifications within the skill of the art are intended to be covered by the appended claims.

Having described the invention, the following is claimed:

1. A neurostimulator delivery apparatus comprising:
   a handle portion;
   an elongated shaft extending from said handle portion;
   a distal deployment portion configured to releasably mate with a neurostimulator, wherein the neurostimulator is sized and configured for implantation into a pterygopalatine fossa (PPF) in a craniofacial region of a subject; and
   a hub portion formed between said elongate shaft and said distal deployment portion, the hub portion comprising:
   a lower surface extending along a first plane and integrally formed with oppositely disposed side walls;
   at least one tang comprising an overhang portion extending along a second plane, the overhang portion being configured to engage a top portion of the neurostimulator such that the neurostimulator is retained substantially underneath the overhang portion and provide a retention force against the neurostimulator proximally towards the handle portion; and
   a wall interconnecting the lower surface and the overhang portion and extending substantially perpendicular to the first plane and the second plane.

2. The neurostimulator delivery apparatus of claim 1, wherein the neurostimulator is sized and configured for implantation on a posterior maxilla.

3. The neurostimulator delivery apparatus of claim 1, wherein the neurostimulator further comprises:
   a stimulator body;
   an integral stimulation lead including one or more stimulating electrodes; and
   an integral fixation apparatus configured to be formed around a zygomaticomaxillary buttress.

4. The neurostimulator delivery apparatus of claim 2, wherein the neurostimulator is configured to lay flat against a posterior maxilla, and the stimulation lead is angled so as to maintain contact with the posterior maxilla as it extends to the PPF.

5. The neurostimulator delivery apparatus of claim 2, wherein the stimulation lead is sized and configured to pass through a lateral opening of the PPF.

6. The apparatus of claim 1, wherein the distal deployment portion has an arcuate shape.

7. The apparatus of claim 1, wherein said hub portion further comprises a port configured to slidably receive a stimulator body of the neurostimulator.

8. The apparatus of claim 1, wherein the at least one tang is a plurality of tangs.

9. A neurostimulator delivery apparatus comprising:
   a handle portion;
   an elongated shaft extending from said handle portion;
   a distal deployment portion;
   a hub portion formed between said elongate shaft and said distal deployment portion, said hub portion being sized and configured to releasably mate with a neurostimulator; wherein the neurostimulator is sized and configured for implantation into a pterygopalatine fossa (PPF) in a craniofacial region of a subject;
   a spine member extending from and having a proximal end securely connected to said hub portion; and
   a sheath securely disposed about a portion of said spine member, said sheath including a splittable seam, the sheath assuming an un-split configuration in a non-deployed configuration and a split configuration upon application of force to the handle portion of the neurostimulator delivery apparatus to release the neurostimulator.

10. The apparatus of claim 9, wherein said sheath further includes a tapered distal end portion that is unsupported by said spine member.

11. The apparatus of claim 9, wherein said sheath further comprises a first lumen configured to receive said spine member and a second lumen configured to receive an integral stimulation lead of the neurostimulator.

12. The apparatus of claim 9, where said spine member is malleable.

* * * * *